(12) United States Patent
Rosenberg (10) Patent No.: US 7,234,934 B2
(45) Date of Patent: Jun. 26, 2007

(54) COMPUTER CONFIGURED APPLIANCE FOR ORTHODONTIC CORRECTION OF MALOCCLUSIONS

(76) Inventor: Farel Rosenberg, 9305 Beverly Crest Dr., Beverly Hills, CA (US) 90210

( * ) Notice: Subject to any disclaimer, the term of this patent is extended or adjusted under 35 U.S.C. 154(b) by 0 days.

(21) Appl. No.: 11/299,616

(22) Filed: Dec. 12, 2005

(65) Prior Publication Data

US 2006/0093984 A1 May 4, 2006

Related U.S. Application Data

(63) Continuation-in-part of application No. 10/263,611, filed on Oct. 4, 2002, now abandoned.

(51) Int. Cl.
*A61C 7/00* (2006.01)
(52) U.S. Cl. ............................................. 433/6
(58) Field of Classification Search .................... 433/6, 433/7, 9, 24
See application file for complete search history.

(56) References Cited

U.S. PATENT DOCUMENTS 3,464,114 A * 9/1969 Brader ......................... 433/10
5,055,039 A * 10/1991 Abbatte et al. ............... 433/24
5,059,118 A * 10/1991 Breads et al. ................. 433/6
6,554,613 B1 * 4/2003 Sachdeva et al. ............. 433/24

* cited by examiner

*Primary Examiner*—Melba Bumgarner
(74) *Attorney, Agent, or Firm*—Albert O. Cota (57) ABSTRACT

A computer configured appliance (10) that applies amplified leverage for orthodontic correction of malocclusions that incorporates a number of computer configured prong units (20) for attachment to selected teeth. Each prong unit (20) is connected to a detachable placement template (28) for positioning the prong units (20) at a computer selected tooth location. Once positioned, the prong units (20) are bonded with dental bonding cement (40) to a predetermined site of each tooth. A successive series of computer configured segmented compartment arches (42) are connected by interproximal material (48), with each arch having elastic entry compartments (38), are snapped onto each prong unit (20). When each arch (42) has achieved the optimum tooth movement, the arch (42) is unsnapped, removed and replaced by snapping in the next arch in the series, which has a higher sequential increment of movement.

15 Claims, 6 Drawing Sheets

COMPUTER CONFIGURED APPLIANCE FOR ORTHODONTIC CORRECTION OF MALOCCLUSIONS

CROSS REFERENCE TO RELATED APPLICATION

This application is a continuation-in-part of application Ser. No. 10/263,611 filed Oct. 4, 2002 now abandoned.

TECHNICAL FIELD

The invention generally pertains to orthodontic treatment of maloccluded teeth, and more specifically to a computer configured appliance that attaches the lingual or labial side of each tooth to a series of segmented compartment arches that are worn to apply the necessary force to achieve and control the involuntary movement of the teeth over a period of time.

Background Art

Previously, many types of appliances, positioners, retainers, etc. have been used to provide an effective means for the treatment of malocclusion.

The prior art listed below did not disclose any patents that possess the novelty of the instant invention, however the following U.S. patents are considered related:

| Patent Number | Inventor | Issue Date |
|---|---|---|
| 4,657,508 | Dellinger | Apr. 14, 1987 |
| 4,793,803 | Martz | Dec. 27, 1988 |
| 4,856,991 | Breads et al. | Aug. 15, 1989 |
| 5,055,039 | Abbatte et al. | Oct. 8, 1991 |
| 5,378,001 | Tepper | Dec. 27, 1994 |
| 6,027,340 | Chun | Feb. 22, 2000 |
| 6,884,067 | Tuneberg | 26 Apr. 2005 |
| 6,190,166 | Sasakura | 20 Feb. 2001 |
| 5,791,896 | Ipenburg | 11 Aug. 1998 |
| 3,896,549 | Wallshein | 29 Jul. 1975 |

Dellinger in U.S. Pat. No. 4,657,508 utilizes a bracket having a non-conforming base portion that is mounted to a tooth in a preestablished position and angular orientation using a contoured shim and head opposite to the base. The head includes a slot capable of receiving a conventional arch wire. A fixture is formed to fit over a tooth replica of which a bracket and shim is affixed. The fixture is rigid and made of a material that can be changed to a non-rigid state upon application of a state-changing medium. The completed bracket and shim is attached to a tooth and bonded thereunto.

U.S. Pat. No. 4,793,803 issued to Martz teaches an orthodontic appliance which is insertable and removable from a patient and consists of a rigid portion that mates with the tooth surface. An intermediate flexible portion interposed between the rigid portion and the tooth biases the teeth into the desired position. The rigidity of the rigid portion varies depending on the condition of the individual tooth.

Breads et al. in U.S. Pat. No. 4,856,991 discloses a finishing positioner to which is secured coupling members having portions protruding from the sides. The positioner consists of an arcuate body of an elastomer base material that is positioned about the teeth, and coupling members of at least one dental arch defining a recess for receiving the teeth. A series of indentations are disposed across the tooth engaging surfaces that are shaped to accept a corresponding coupling member. The positioner is constructed by forming a model repositioning the teeth as a standard.

Abbatte et al. in U.S. Pat. No. 5,055,039 teaches an orthodontic positioned appliance made of elastomer base material that is formed directly on tooth coupling members during fabrication. A construction model that is corrected to the desired orientation provides an exact adaptation to assure maximum purchase with the teeth. A first form of a strip of elastomer material has recesses in spaced relation for snap fitting onto the members, with the positioner urging the patient's teeth into an exact fit therebetween. A second form is molded to provide an arcuate body of elastomer with a trough for receiving teeth with side walls and recessed in a spaced relationship.

U.S. Pat. No. 5,378,001 issued to Tepper is for an orthodontic appliance having a labial arch wire connected to a pair of clasps that are seated over several midregion teeth. A pair of structural braces attach the clasps to a lingual arch wire made of memory metal to optimize the force of the arch shape. A bridge that is formed of a radial loop of memory metal exerts persistent linear force to the teeth in the opposite direction of a deformation.

Chun in U.S. Pat. No. 6,027,340 discloses an orthodontic appliance comprised of an upper splint having tooth sockets for retention of the upper set of teeth, and a lower splint with sockets and a pair of elastic linkages connecting therebetween.

For background purposes and as indicative of the art to which the invention is related reference may be made to the remaining cited patents found in the search.

DISCLOSURE OF THE INVENTION

Wire bending in classic orthodontic practice is a time consuming but essential component of many treatment procedures. Tooth alignment problems are corrected by applying appropriate bends to a generally U-shaped arch wire. Misaligned teeth are attached to the arch wire by means of orthodontic brackets whose wire receiving slots are used as attachment points, which allows forces to arise which result in a desired reorientation of the teeth over a period of time. The misaligned teeth are tied to portions of the arch wire, which serve to define the proper orientation.

The modes of tooth movement required for misalignment correction are: up-down (extrusion or intrusion), in-out (both movements towards the tongue and towards the cheek side of the mouth), rotation (turning of the tooth in its socket clockwise or counterclockwise), angulation (tilting of the tooth mesially or distally), torque (twisting of the tooth towards the tongue or cheek side of the mouth), and side-to-side tooth movement (lateral).

Present day orthodontic brackets are applied to the teeth by cementing. Each bracket is provided with a slot for holding the arch wire, and top and bottom grooves and tie wings for holding tie wires, the latter being used for binding the brackets to the arch wire. In older techniques, the brackets were first welded to metal bands, the latter were then slipped over individual teeth and cemented in place.

One-piece orthodontic brackets are cast or molded to exert a fixed ("average") amount of up-down, in-out, sideto-side, angulation, rotation, or torque force. This is done to reduce the extent of manual manipulation of the arch wires.

Since provision has been made for "average" teeth in these fixed systems, there is no allowance for normally occurring differences in dental anatomy or bracket placement errors. Arch wire bending is required to correct the fine alignment problems. Time consuming, expensive iterations are therefore required.

An improved currently available method that eliminates wire bending in orthodontic practice by utilizing a series of miniature tooth positioners that are made with the aid of a computer. This method moves teeth in small increments and requires 22-hours per day of voluntary use. The theory behind this series of positioners is based on the natural anatomy of the teeth, i.e. undercuts of the dentition. The method is slow, relatively inefficient, non-retentive and very limited in its usage.

The primary object of the present invention is to utilize new methodology to achieve and control involuntary tooth movement 24-hours a day. A separate attachment device on each tooth is lingual side greatly amplifies the mechanical force applied to that tooth. Each attachment device consists of a prong unit with a bonded base, a neck and a head that is configured square, triangular or irregular. The device is in a computer selected form for each tooth based on models and impressions that were previously made. A second part of the invention consists of a segmented compartment arch which is also fabricated with computer assistance. The arch includes a series of hollow chambers that are spaced along the arch and connected by interproximal material so as to be in close proximity to the intended prong unit. Depending on its orientation and position along the arch, each chamber is capable of exerting force on each tooth that is a carrying prong head: in-out, up-down, angulation, rotation, torque and side-to-side directions.

After a patient has worn the initial arch for a period of time, partial orthodontic movement is achieved. It is a relatively simple procedure to replace the first arch with the next sequentially configured arch by simply unsnapping the prong units and snapping in a new arch. This procedure continues the tooth movement in the next arch increment. When the pre-prepared series of arches have all been utilized, the orthodontic procedure is completed. Because the prong head device exerts a much higher leverage on each tooth than the previously described tooth positioners, the present invention is efficient, capable of handling complex cases, and able to produce detailed and specific individual tooth movement.

Another advantage of the present invention is the lower cost and ease of use which will lead to increased patient satisfaction.

Further, advantages of the present invention include the elimination of orthodontic wires, ligations and other time-consuming appliances that are now required in orthodontics while achieving complex corrections with high precision.

Another object of the present invention is its ability to move teeth without patient cooperation. Further, the installation of the invention on the lingual side of a tooth makes wearing more comfortable and provides low visibility. It should be noted however that the invention may be used on the labial side of the tooth when cosmetic concerns are not important.

These and other objects and advantages of the present invention will become apparent from the subsequent detailed description of the preferred embodiment and the appended claims taken in conjunction with the accompanying drawings.

BEST MODE FOR CARRYING OUT THE INVENTION

Figure 5:
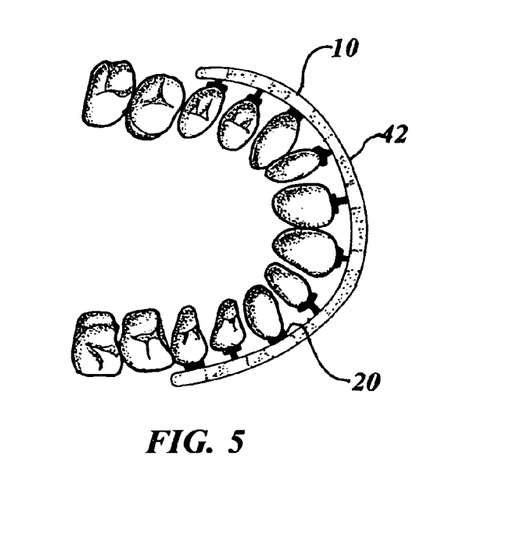
FIG. 5 is a plan view of a patient's lower dental arch as viewed from the inside of the mouth with the computer configured appliance attached to the prong units on the labial side of the teeth.
Figures 6, 7, 8, 9, 10, 11, 11A:
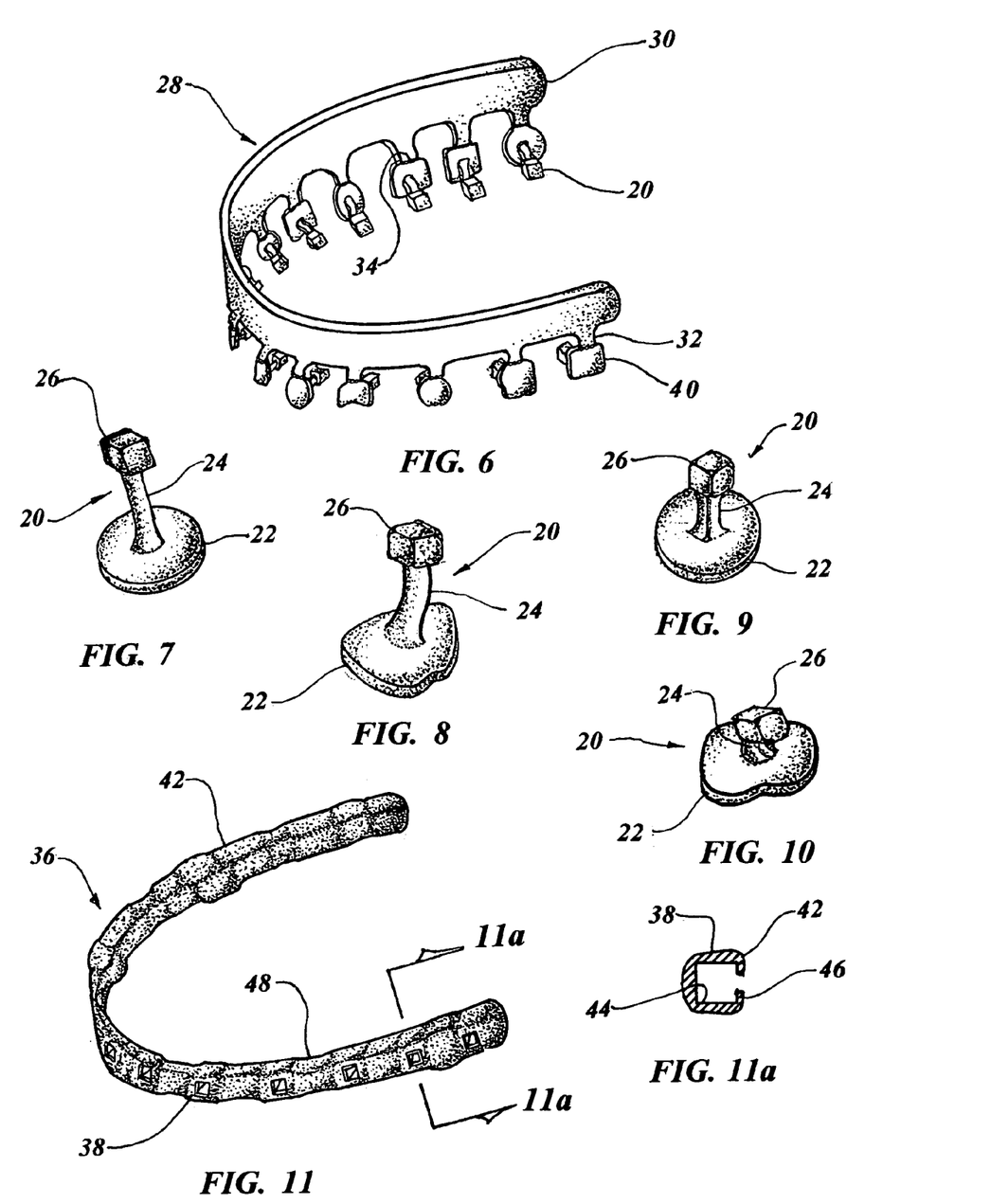
FIG. 6 is a perspective view of one embodiment of the placement template ready to be inserted adjacent to a patient's lower dental arch for cementing the prong units in place.
FIG. 7 is a partial isometric view of a typical embodiment of one of the prong units illustrating a round representative shape of the prong base.
FIG. 8 is a partial isometric view of a typical embodiment of one of the prong units illustrating another representative shape in the form of an irregular base with a round bent neck.
FIG. 9 is a partial isometric view of a typical embodiment of one of the prong units illustrating yet another representative oval shaped base with a square straight neck.
FIG. 10 is a partial isometric view of a typical embodiment of one of the prong units illustrating still another representative irregular shaped base and a shortened bent neck
FIG. 11 is a perspective view of a typical computer configured segmented compartment arch the preferred embodiment.
FIG. 11a is a cross-sectional view taken along the lines 11a-11a of FIG. 11.
Figure 12:
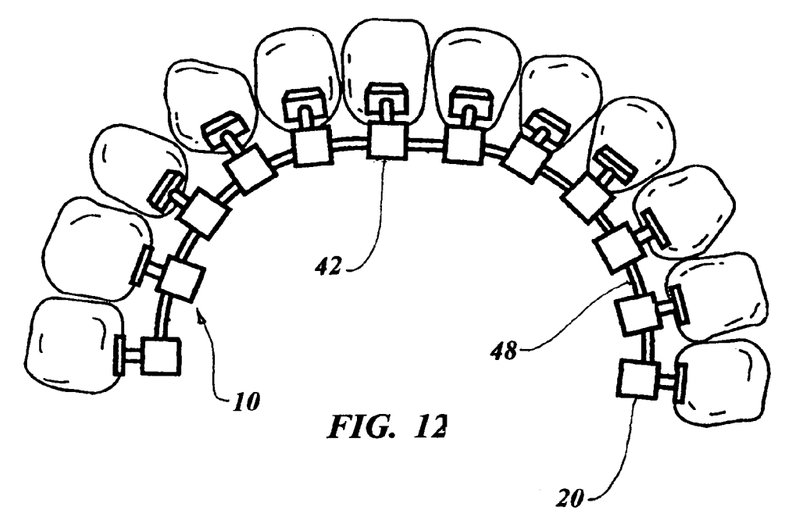
FIG. 12 is a plan view of a dental arch with a "beginning" segmented compartment arch in place. The corrective forces generated by this particular arch are only the first of a sequence of orthodontic treatments continued by sequential computer-designed arches. The removal and substitution of the arches is made relatively simple by the use of the retentive flexible lips framing each elastic entry compartment opening.

The best mode for carrying out the invention is presented in terms of a preferred embodiment for a computer configured appliance 10, which is preferably attached to the lingual side of a person's tooth. A second embodiment utilizes the same basic computer configured appliance 10 except it is attached to the labial side of the person's tooth. The preferred embodiment, as shown in FIGS. 1, 2, and 4 through 21, is comprised of the computer configured appliance 10 that is used for orthodontic correction of malocclusions. A plurality of prong units 20 are provided for attachment to selected teeth. Each prong unit 20 consists of a base 22, a neck 24 and a multisided head 26, as illustrated removed from the invention in FIGS. 7-10. In order to provide the desired correction factors to each tooth, the prong unit 20 must be configured separately to fit the contour of each tooth and to provide the necessary attachment interface to urge the tooth into the corrected orientation. In order to provide the necessary attachment interface, the base 22 attached directly onto the tooth may be round, oval, square, rectangular, polygonal, triangular or irregular according to the mating surface of the tooth. FIGS. 7-9 depict only a few options, as a myriad of shapes may be computer selected and the face surface of the base 22 relative to the neck 24 and head 26 may be positioned straight or with an angular orientation.

Figure 1:
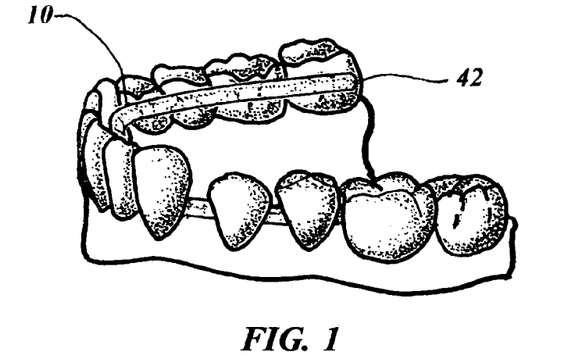
FIG. 1 is a perspective view of a patient's lower dental arch with the computer configured appliance attached to the lingual side of the teeth in the preferred embodiment.
Figure 2:
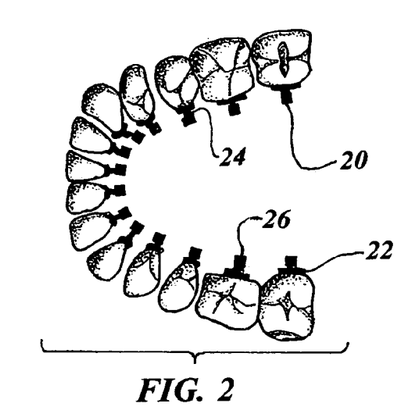
FIG. 2 is a plan view of a patient's lower dental arch as viewed from the inside of the mouth with the prong units cemented in place on the lingual side of the teeth.
Figure 4:
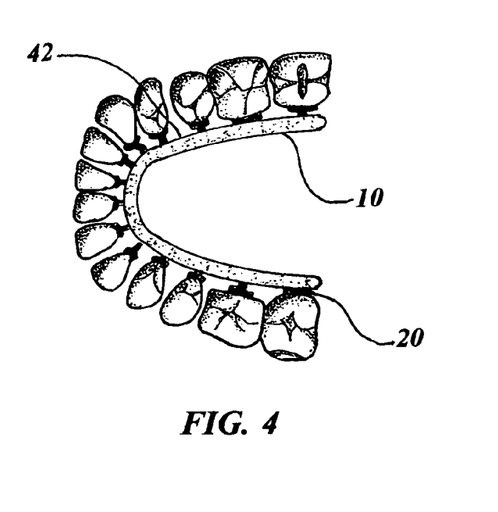
FIG. 4 is a plan view of a patient's lower dental arch as viewed from the inside of the mouth with the computer configured appliance attached to the prong units on the lingual side of the teeth in the preferred embodiment.

The prong unit neck 24 has a computer selected configuration that may be round, square, oval or rectangular, with a length and angular displacement dependent upon each tooth orientation. FIGS. 1, 2 and 4 illustrate the need for length and angular differences as the dental arch of each person varies considerably.

The prong unit multisided head 26 may have any consistent form, however a cube shape is preferred, with each head 26 having the same configuration. Since the preferred configuration is in the form of a cube with all sides identical, it is easy to permit forces to be transmitted to the teeth for position correction. Further, the cube may have sharp or rounded edges and/or corners as long as there is sufficient surface to achieve a firm grip.

The prong unit 20 may be made of any suitable substance, such as a metal or a thermoplastic. The thermoplastic material should have a good balance of tensile strength, surface hardness, rigidity and non-allergenic properties, and obviously compatibility for use in conjunction with a human body.

Figure 3:
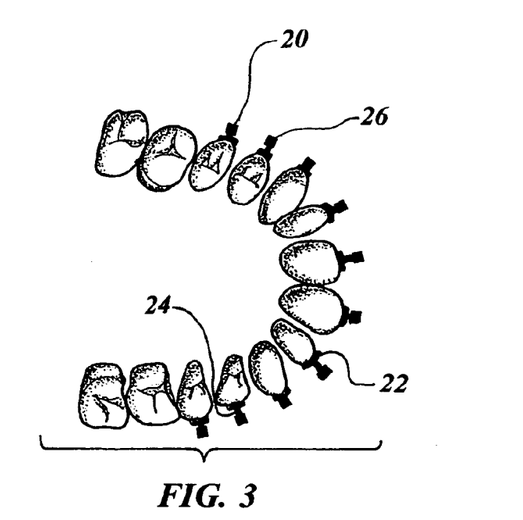
FIG. 3 is a plan view of a patient's upper dental arch as viewed from the inside of the mouth with the prong units cemented in place on the labial side of the teeth.

As previously stated, the preferred embodiment of the invention attaches the prong units to the lingual side of each tooth, as shown in FIGS. 1, 2 and 4, which offers many advantages, particularly on the upper dental arch which is invisible. It is also feasible to attach the prong units 20 to the labial side of each tooth, as depicted in FIGS. 3 and 5, with a combination of upper and lower prong placement also being a viable consideration.

In order to orient the prong units 20 onto the teeth in an arrangement that creates a datum point for further attachment of the prong unit heads 26, a placement template 28 is utilized. The template 28 permits retainment and detachment of the prong units 20, which allows accurate positioning of each prong unit on a selected tooth. There are a number of construction methods for producing the placement template 28, such as a computer configured connecting arched band 30, as shown in FIG. 6. The connecting arched band 30 is comprised of a ribbon of thermoplastic material that is cambered to mate with a person's dental arch and uncorrected teeth, with the band 30 having extended positioning tabs 32 for attachment of the prong unit base 22. This arrangement includes means for removing the connecting arched band 30 from each prong unit after bonding to each tooth. The removal means are comprised of a plurality of perforations 34 that are located on the extended positioning tabs 32, thereby allowing the attached prong units 20 to be broken off individually. Any sharp edges that remain on the prong unit heads 26 may be ground smooth by the dental practitioner after final attachment.

An alternative embodiment of the placement template 28 is a computer configured template segmented compartment arch 36, similar to the illustration of FIG. 11. The template segmented compartment arch 36 includes a plurality of elastic entry compartments 38 for containing the prong units 20, which permit removal after bonding from each tooth by unsnapping each prong unit 20 individually.

The prong units 20 incorporate positioning means for bonding individual prong units 20 to a predetermined site of each selected tooth. The bonding means typically is comprised of dental bonding cement 40 that is applied between the bottom of the prong base and the tooth surface to assure a durable purchase. The dental bonding cement is well known in the dental art and is in constant usage throughout the world.

To complete the appliance 10 a successive series of computer configured segmented compartment arches 42 are used either on the lingual side or the labial side of the teeth. Each segmented compartment arch 42 includes a plurality of elastic entry compartments 38 that are snapped over the prong units 20, thereby selectively repositioning individual teeth when utilized incrementally in a timely sequence. The elastic entry compartments 38, as shown in FIG. 11a, include hollow chambers 44 with elastic lips 46 on the entry periphery. The elastic lips 46 are dimensioned to intimately engage the heads 26 of the prong units 20, thus providing a firm grip that permits directional forces to be exerted on the teeth.

Each segmented compartment arch 42 contains computer configured inter-proximal material 48 that is disposed between each entry compartment 38 to provide varied correctional forces on the prong units 20. The inter-proximal material 48 may be a flexible resilient substance that is suitable for providing up-down, in-out, side-to-side, angulations, rotation, and torque forces to achieve correction of misaligned teeth. The inter-proximal material 48 between entry compartments 38 can also consist of a semi-rigid substance having the capability to provide contraction and expansion forces to achieve correction of misaligned teeth.

The invention utilizes the series of segmented compartment arches 42 that are worn by the patient for a period of time and that are discarded with the next arch 42 configured to transmit the next increment of corrective force to each misaligned tooth. After a period from two to five weeks of wearing a specific arch 42, it is unsnapped and replaced with the next, sequential arch, which includes computer derived changes for achieving a subsequent increment of tooth movement.

This sequence is repeated until final, satisfactory tooth alignment has been achieved, at which time the orthodontic correction is completed. After the last arch 42 has been discarded the prong heads 20 are removed. A clear plastic aligner well known in the art, may then be worn if needed, for a short time to further stabilize the correction and prevent relapse.

It should be noted that the template segmented compartment arch 36 previously described may simply be the first arch 42 without the corrective alignment in the compartments 38.

Figure 13:
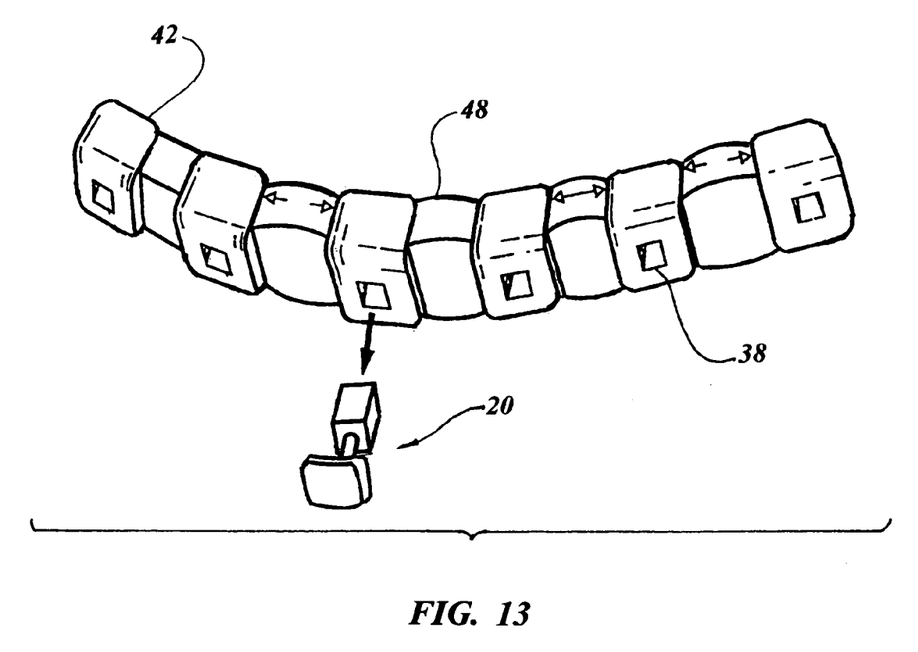
FIG. 13 is an isometric view of the invention similar to that shown in FIG. 12 but employing semi-rigid inter-proximal material used to fill in the spaces between the elastic entry compartments. After the inter-proximal material is compressed, and the prong heads are inserted in their corresponding positions, lateral tooth-separation force vectors are exerted on the teeth.

The inter-proximal material 48 may be semi-flexible or rigid and varied in thickness, shape and composition of material to achieve the desired force generation. The inter-proximal material 48 may also be compressible material, as shown in FIG. 13, which forces the compartments 38 apart, or extensible material, as shown in FIG. 14, which stretches to pull the compartments 38 together.

Figure 14:
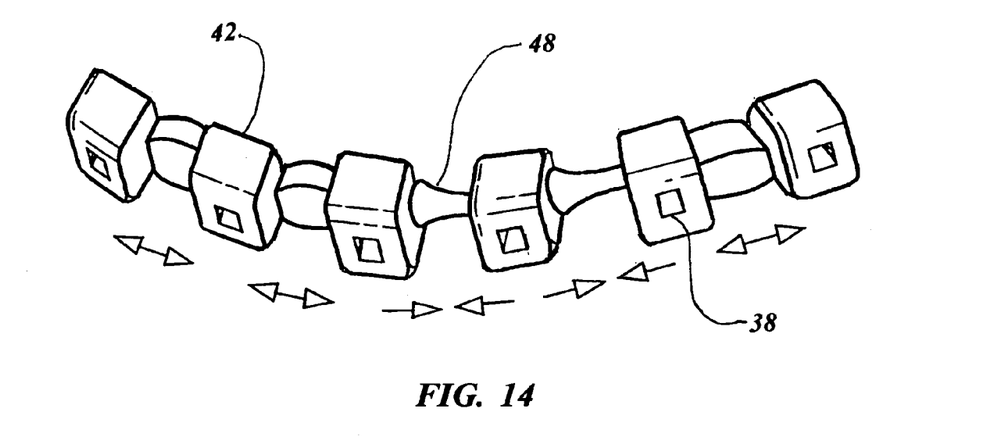
FIG. 14 is an isometric view showing the use of semi-rigid inter-proximal block inserts between elastic entry compartment, which must be stretched to properly engage the prong heads, thus creating lateral tooth-closing forces, as well as compressive type inter-proximal block, which generate expansive tooth-to-tooth forces.
Figure 15:
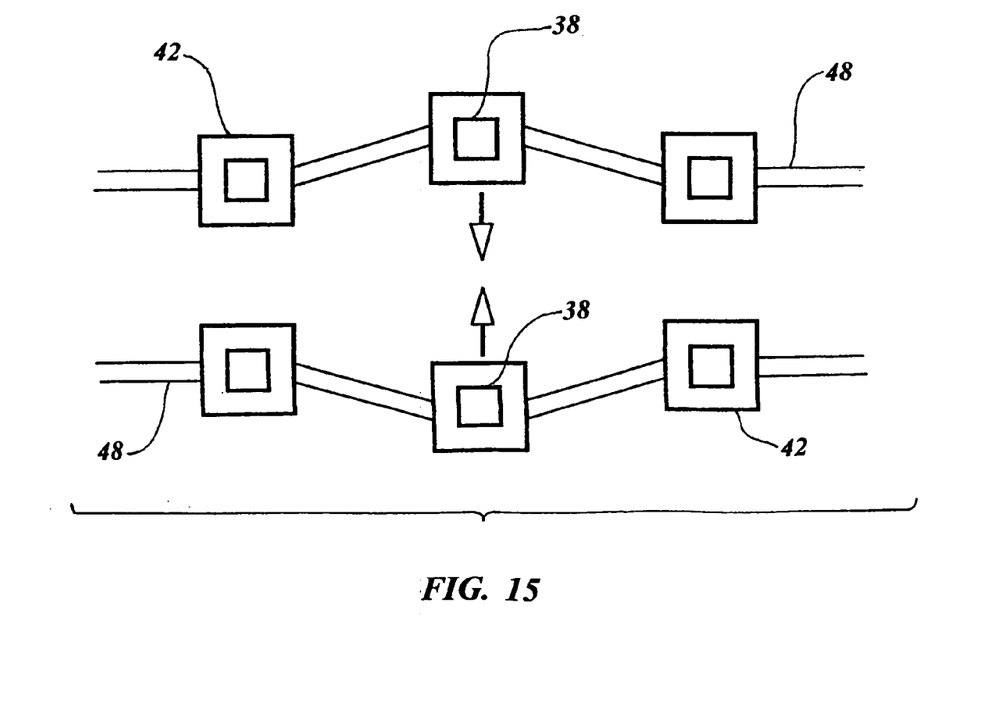
FIG. 15 schematically illustrates up and down motion formed by the segmented compartment arch.
Figure 16:
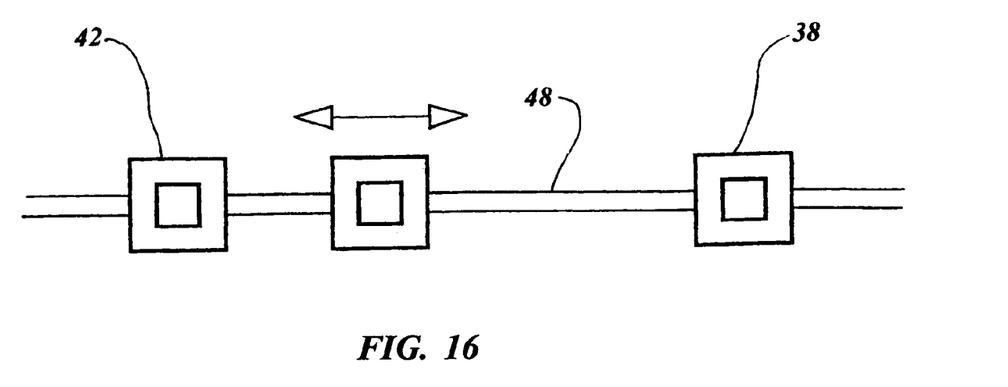
FIG. 16 schematically illustrates side-to-side motion formed by the segmented compartment arch.
Figure 17:
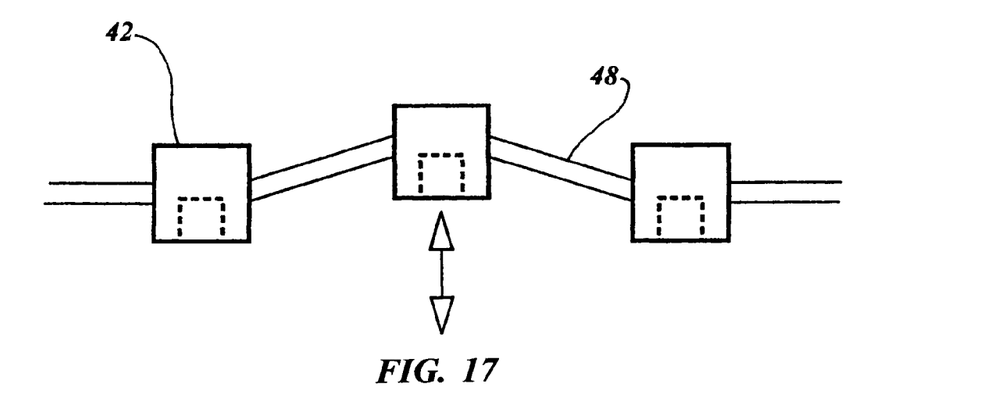
FIG. 17 schematically illustrates in and out motion formed by the segmented compartment arch.
Figure 18:
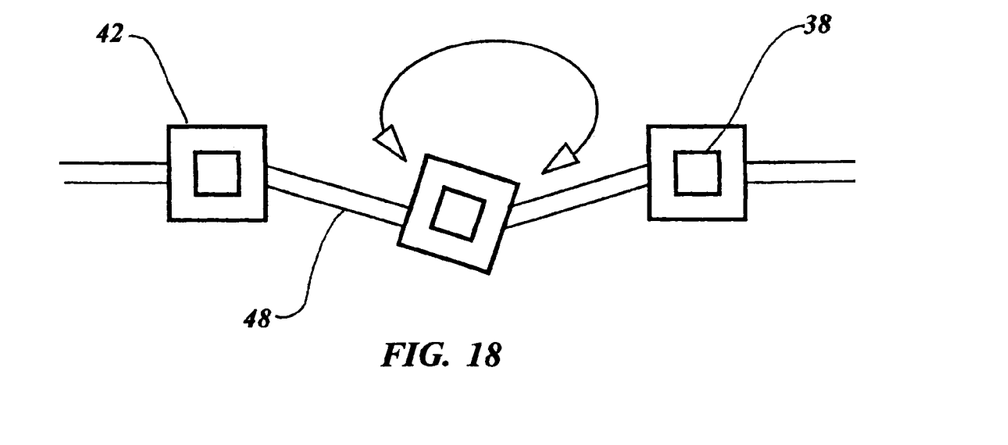
FIG. 18 schematically illustrates angulation's formed by the segmented compartment arch.
Figure 19:
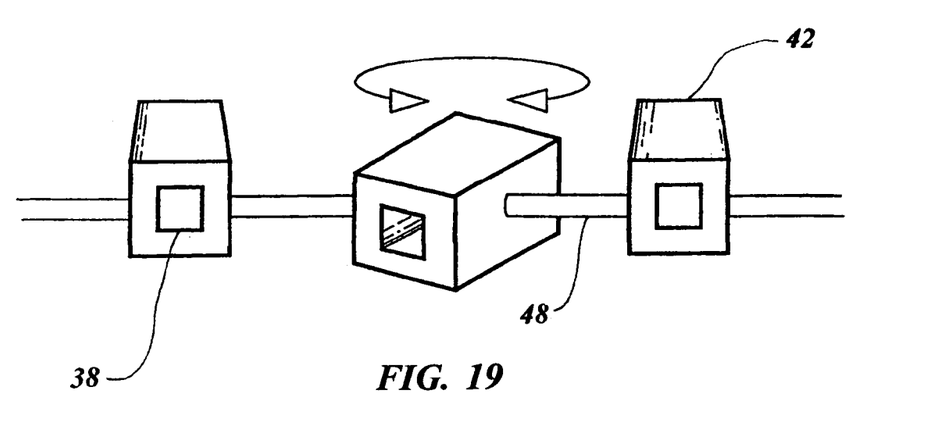
FIG. 19 schematically illustrates rotation formed by the segmented compartment arch.
Figure 20:
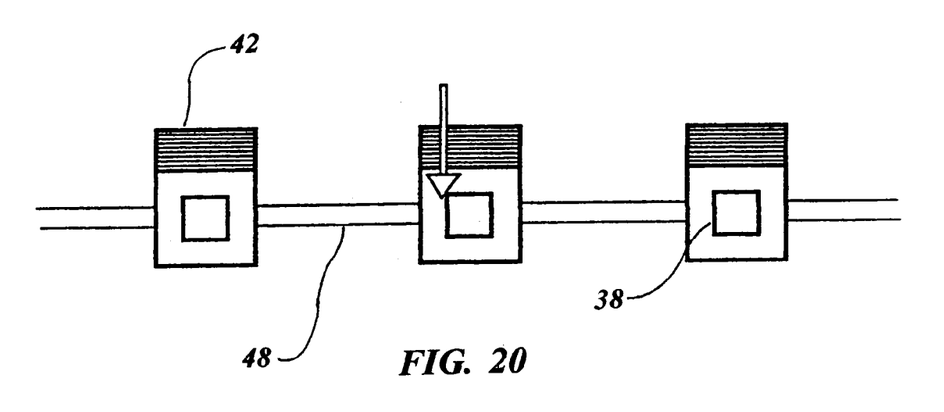
FIG. 20 schematically illustrates outward torque formed by the segmented compartment arch.
Figure 21:
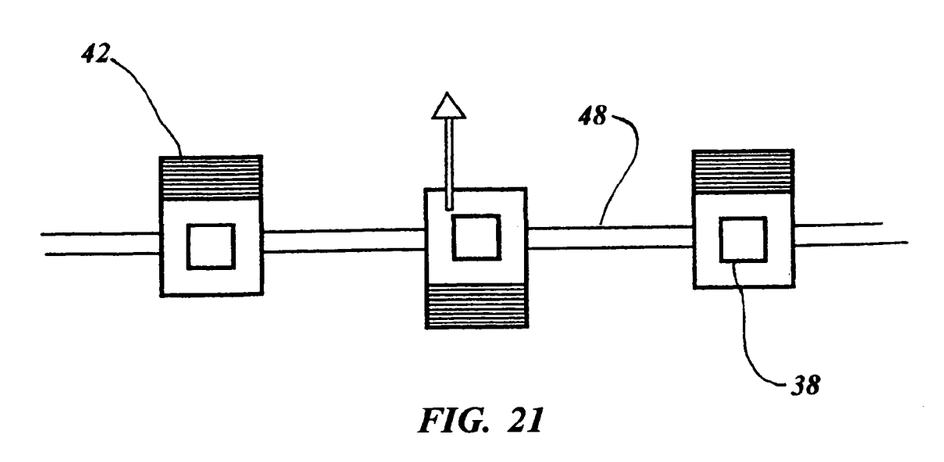
FIG. 21 schematically illustrates inward torque formed by the segmented compartment arch.

The operating principle of the invention may be further explained by the use of the schematic drawings of FIGS. 14-21, in which the entry compartments 38 are represented by squares, the elastic lips 46 represented by smaller squares, and the inter-proximal material 48 represented by horizontal lines. The retention feature may be increased by the use of a circular opening if desired. FIG. 14 represents lateral forces on a tooth, FIG. 15 represents the generation of up and down forces on a tooth, FIG. 16 shows the generation of side-to-side forces on a tooth, FIG. 17 is a top view of in and out forces, FIG. 18 shows angulation forces, FIG. 19 shows rotation forces, FIG. 20 shows downward twisting torque, and FIG. 21 shows the generation of upward twisting torque.

The computer program that selects the configuration of the placement template 28, prong units 20 and segmented compartment arches 42 was previously developed for a similar utility and is known in the art and in present usage. With slight modifications to the existing program the computer selects the optimum configuration for the above elements by comparing the position of a person's teeth from an impression furnished by the dental practitioner to a recognized optimal occlusion. The prong unit 20 shape is established by the computer as to the direction of movement of each individual tooth to achieve the desired ultimate position. The basic shape and material of each segmented compartment arch 42 is determined by the increment of movement required in sequence for each arch 42, which may involve as few as 10, or less, and as many as necessary, which could be 30 or more.

While the invention has been described in detail and pictorially shown in the accompanying drawings, it is not to be limited to such details, since many changes and modifications may be made to the invention without departing from the spirit and scope thereof. Hence, it is described to cover any and all modifications and forms which may come within the language and scope of the appended claims.

The invention claimed is:

1. A computer configured appliance for orthodontic correction of malocclusions which comprises:
   a) a plurality of prong units for attachment to selected teeth,
   b) a detachable placement template connected to each prong unit for positioning the prong units at a computer determined tooth location, said placement template having a computer configured connecting arched band comprising a ribbon of thermoplastic material that is cambered to mate with a person's dental arch and uncorrected teeth, with said band having extended positioning tabs for attachment of the prong units,
   c) means for bonding said prong units to a predetermined site of each tooth, and
   d) a successive series of computer configured segmented compartment arches, with each having elastic entry compartments for snapping each prong unit in place after each prong unit has been bonded to a tooth, thereby selectively positioning each individual tooth sequentially over a period of time.

2. A computer configured appliance for orthodontic correction of malocclusions which comprises:
   a) a placement template having a plurality of detachable prong units that are oriented to position each prong unit on a selected tooth, wherein said placement template having a computer configured connecting arched band comprising a ribbon of thermoplastic material that is cambered to mate with a person's dental arch and uncorrected teeth, with said band having extended positioning tabs for attachment of the prong units,
   b) means for bonding individual prong units to a predetermined site of each selected tooth,
   c) means for removing said placement template connecting arched band from each prong unit after bonding to each tooth, and
   d) a successive series of computer configured segmented compartment arches, with each having a plurality of elastic entry compartments that are snapped over said prong units for selectively repositioning individual teeth when utilized incrementally in a timely sequence.

3. The computer configured appliance as recited in claim 2 wherein said detachable prong units each further comprises a base, a neck and a multisided head.

4. The computer configured appliance as recited in claim 3 wherein said prong unit base further comprises a configuration selected from the group consisting of round, oval, square, rectangular, polygonal and triangular, and having a surface relative to the neck and head at an angular orientation.

5. The computer configured appliance as recited in claim 3 wherein said prong unit neck further comprises a configuration selected from the group consisting of round, square, oval and rectangular, with a length and angular displacement dependent upon tooth orientation.

6. The computer configured appliance as recited in claim 3 wherein said prong unit multisided head further comprises a cube shape, with each head having the same configuration.

7. The computer configured appliance as recited in claim 2 wherein each said prong unit further comprises a metal or a thermoplastic construction.

8. The computer configured appliance as recited in claim 2 wherein each said prong unit is provided for bonding to a lingual side of a tooth.

9. The computer configured appliance as recited in claim 2 wherein each said prong unit is provided for bonding to a labial side of a tooth.

10. The computer configured appliance as recited in claim 2 wherein said means for bonding individual prong units to a predetermined side of each selected tooth comprises bonding with cement to assure a durable purchase.

11. The computer configured appliance as recited in claim 2 wherein said computer configured segmented compartment arches with each having a plurality of elastic entry compartments further comprises said elastic entry compartments defining hollow chambers with elastic lips on an entry periphery.

12. The computer configured appliance as recited in claim 2 wherein each computer configured segmented compartment arch further comprises a computer configured inter-proximal material that is disposed between each entry compartment for providing varied correctional forces on the prong units.

13. The computer configured appliance as recited in claim 12 wherein said inter-proximal material between entry compartments further comprises a flexible substance having a resilience suitable to provide up-down, in-out, side-to-side, angulations, rotation, and torque forces to achieve position correction of misaligned teeth.

14. The computer configured appliance as recited in claim 12 wherein said inter-proximal material that is disposed between each entry compartment further comprises a semi-rigid substance having the capability to provide contraction and expansion forces to achieve correction of misaligned teeth.

15. A computer configured appliance for orthodontic correction of malocclusions which comprises:
   a) a placement template having a plurality of detachable prong units that are oriented to position each prong unit on a selected tooth, wherein said placement template having a plurality of extended positioning tabs each having a plurality of perforations that permits removal of the prong units by breaking the attached prong units off individually,
   b) means for bonding individual prong units to a predetermined site of each selected tooth,
   c) means for removing a placement template connecting arched band from each prong unit after bonding to each tooth, and
   d) a successive series of computer configured segmented compartment arches, with each having a plurality of elastic entry compartments that are snapped over said prong units for selectively repositioning individual teeth when utilized incrementally in a timely sequence.

* * * * *